(12) United States Patent
Wingen

(10) Patent No.: US 6,482,478 B1
(45) Date of Patent: Nov. 19, 2002

(54) FLUORINATED DERIVATIVES OF PHENANTHRENE AND THE UTILIZATION THEREOF IN LIQUID CRYSTAL MIXTURES

(75) Inventor: Rainer Wingen, Hattersheim (DE)

(73) Assignee: Aventis Research & Technologies GmbH & Co. KG, Frankfurt am Main (DE)

(*) Notice: Subject to any disclaimer, the term of this patent is extended or adjusted under 35 U.S.C. 154(b) by 0 days.

(21) Appl. No.: 09/530,665

(22) PCT Filed: Nov. 5, 1998

(86) PCT No.: PCT/EP98/07080

§ 371 (c)(1),
(2), (4) Date: Sep. 5, 2000

(87) PCT Pub. No.: WO99/24385

PCT Pub. Date: May 20, 1999

(30) Foreign Application Priority Data

Nov. 5, 1997 (DE) .......................................... 197 48 819

(51) Int. Cl.[7] ...................... C09K 10/32; C07C 43/225; C07C 25/13; C07C 23/44
(52) U.S. Cl. .................... 428/1.1; 252/299.62; 570/129; 570/183; 570/187
(58) Field of Search ..................... 428/1.1; 252/299.62; 570/183, 187, 129

(56) References Cited

U.S. PATENT DOCUMENTS

| | | | | |
|---|---|---|---|---|
| 5,447,656 A | * | 9/1995 | Jungbauer et al. ..... | 252/299.01 |
| 5,648,021 A | | 7/1997 | Wingen et al. ........ | 252/299.62 |
| 5,888,422 A | * | 3/1999 | Manero et al. ........ | 252/299.62 |
| 6,168,838 B1 | * | 1/2001 | Schmidt et al. .............. | 428/1.1 |

FOREIGN PATENT DOCUMENTS

| | | |
|---|---|---|
| DE | 3920625 | 1/1991 |
| DE | 195 00 768 | 9/1995 |
| DE | 44 32 970 | 3/1996 |
| EP | 0 032 362 | 7/1981 |
| EP | 0 405 346 | 1/1991 |
| JP | 10-236992 | * 9/1998 |

OTHER PUBLICATIONS

Patent Abstracts of Japan, vol. 98, No. 14, 1998.
Tetrahedron Letters, vol. 34, No. 2, pp. 281–284, 1993.

* cited by examiner

*Primary Examiner*—Shean C. Wu
(74) *Attorney, Agent, or Firm*—Frommer Lawrence & Haug LLP

(57) ABSTRACT

Fluorinated derivatives of phenanthrene, and their use in liquid-crystal mixtures Fluorinated phenanthrene derivatives of the formula (I)

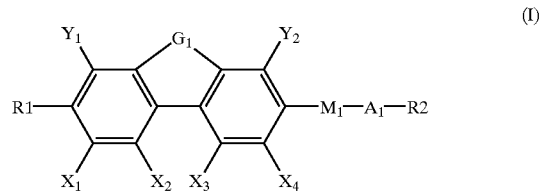

in which
$G_1$ is —CH=CH— or —CH$_2$CH$_2$—
X is H or F
Y is H or F, and
$R^1$ and $M_1$—$A_1$—$R^2$ are mesogenic radicals,
are suitable as components of liquid-crystalline mixtures.

22 Claims, No Drawings

FLUORINATED DERIVATIVES OF PHENANTHRENE AND THE UTILIZATION THEREOF IN LIQUID CRYSTAL MIXTURES

SEQUENCE LISTING

Not Applicable

CROSS-REFERENCE TO RELATED APPLICATION

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

In addition to nematic and cholesteric liquid crystals, optically active tilted smectic (ferroelectric) liquid crystals have also been used recently in commercial display devices.

2. Description of Related Art

Clark and Lagerwall have been able to show that the use of ferroelectric liquid crystals (FLCS) in very thin cells results in opto-electrical switching or display elements which have response times which are faster by a factor of up to 1000 compared with conventional TN ("twisted nematic") cells (see, for example, EP-A 0 032 362). On the basis of this and other favorable properties, for example the possibility of bistable switching and the fact that the contrast is virtually independent of the viewing angle, FLCs are fundamentally highly suitable for areas of application such as computer displays.

The use of FLCs in electro-optical or fully optical components requires either compounds which form tilted or orthogonal smectic phases and are themselves optically active, or the induction of ferroelectric smectic phases by doping compounds, which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 μm) or, even better, is fully compensated (see, for example, T. Matsumoto et al., Proc. of the 6th Int. Display Research Conf., Japan Display, Sep. 30–Oct. 2, 1986, Tokyo, Japan, pp. 468–470; M. Murakami et al., ibid. pp. 344–347). This is achieved, for example, by mixing the chiral liquid-crystal mixture having, for example, a left-handed helix in the N* phase with one or more optically active dopants which induce a right-handed helix, in such amounts that the helix is compensated.

Use of Clark and Lagerwall's SSFLCD (surface-stabilized ferroelectric liquid-crystal display) effect for uniform, planar alignment furthermore requires that the pitch in the smectic C* phase is significantly greater than the thickness of the display element (Mol. Cryst. Liq. Cryst. 1983, 94, 213 and 1984,114, 151).

The optical response time τ[μs] of ferroelectric liquid-crystal systems, which should be as short as possible, depends on the rotational viscosity of the system γ [mPas], the spontaneous polarization $P_S$ [nC/cm$^2$] and the electric field strength E [V/m], in accordance with the equation

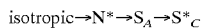

$$\tau \sim \frac{\gamma}{P_s \cdot E}$$

Since the field strength E is determined by the electrode separation in the electro-optical component and by the applied voltage, the ferroelectric display medium must have low viscosity and high spontaneous polarization in order to achieve a short response time.

Finally, in addition to thermal, chemical and photochemical stability, a low optical anisotropy Δn and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA).

The totality of these requirements can only be achieved by means of mixtures of a plurality of components. The base (or matrix) used are preferably compounds which if possible themselves already have the desired phase sequence I→N→$S_A$→$S_C$. Further components of the mixture are frequently added in order to lower the melting point and to broaden the $S_C$ and usually also the N phase, to induce optical activity, for pitch compensation and to match the optical and dielectric anisotropies; however, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B.I. Ostrovski in Advances in Liquid Crystal Research and Applications, Oxford/Budapest, 1980, 469 ff., and the PSFLCD effect is described in DE-A 39 20 625 and EP-A 0 405 346. In contrast to the SSFLCD effect, utilization of these effects requires a liquid-crystalline material having a short $S_C$ pitch.

Fluorinated derivatives of phenanthrene for use in liquid-crystal mixtures are disclosed, for example, in DE-A 195 00 768.

However, since the development, in particular of ferroelectric liquid-crystal mixtures, in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide novel compounds which, in liquid-crystalline mixtures, are suitable for improving the property profile of these mixtures.

BRIEF SUMMARY OF THE INVENTION

Surprisingly, it has been found that fluorinated phenanthrene derivatives of the formula (I) are particularly suitable for use in liquid-crystal mixtures.

BRIEF DESCRIPTION OF SEVERAL VIEWS OF THE DRAWING(S)

Not Applicable

DETAILED DESCRIPTION OF THE INVENTION

The invention therefore relates to Fluorinated phenanthrene derivatives of the formula (I)

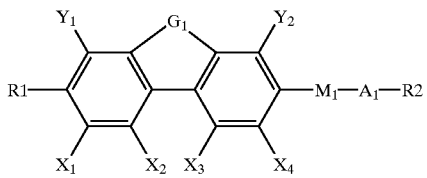

(I)

where the symbols and indices are defined as follows:

$G_1$ is —CH=CH— or —$CH_2CH_2$—;

$X_1$, $X_2$, $X_3$ and X4, independently of one another, are H or F, with the provisos that
  a) $X_1$ and $X_2$, and $X_3$ and $X_4$ are not simultaneously H
  b) $X_1$ and $X_2$, and $X_3$ and $X_4$ are not simultaneously F
  c) at least one X from this group is F;

$Y_1$ and $Y_2$, independently of one another, are H or F;

$R^1$ and $R^2$ are identical or different and are
  a) a straight-chain or branched alkyl radical (with or without an asymmetrical carbon atom) having 1 to 20 carbon atoms, in which, in addition, one or more H atoms may be replaced by F and where
    a1) one or more non-adjacent and non-terminal —$CH_2$— groups may be replaced by —O—, —S—, —CO—O—, —O—CO—, —O—CO—O— or —$Si(CH_3)_2$—, and/or
    a2) one or more —$CH_2$— groups may be replaced by —CH=CH—, —C≡C—, cyclopropane-1,2-diyl, 1,4-phenylene, 1,4-cyclo-hexylene or 1,3-cyclopentylene, and/or
    a3) the terminal —$CH_3$ group may be replaced by one of the following chiral groups (optically active or racemic):

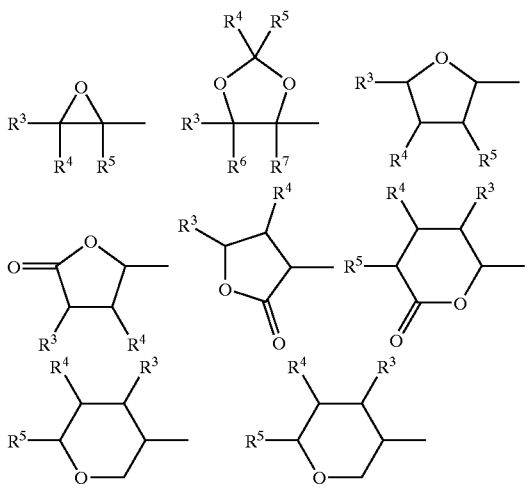

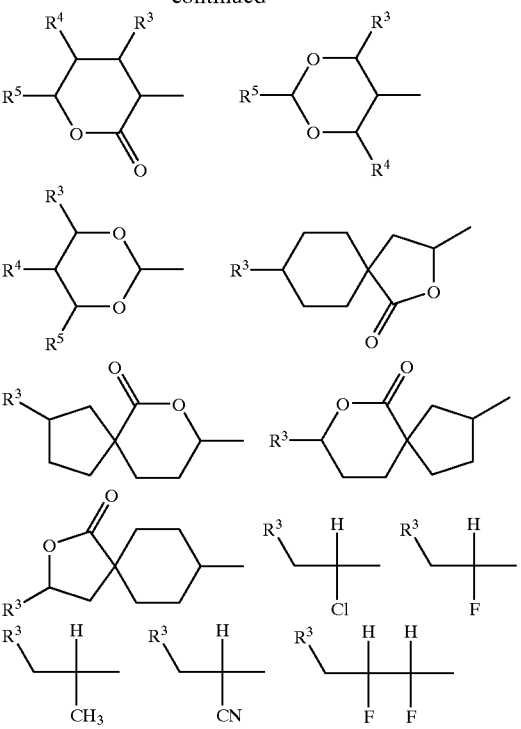

$R^1$ is alternatively hydrogen, —$OCF_3$, —$CF_3$, —CN, —F, —Cl, —$OCHF_2$, —$OCH_2F$, —$CHF_2$ or —$CH_2F$;
  b) $R^1$ is alternatively hydrogen, Cl or F;

$R^3$, $R^4$, $R^5$, $R^6$ and $R^7$ are identical or different and are
  a) hydrogen
  b) a straight-chain or branched alkyl radical (with or without an asymmetrical carbon atom) having 1 to 16 carbon atoms, where
    b1) one or more non-adjacent and non-terminal —$CH_2$— groups may be replaced by —O—, and/or
    b2) one or two —$CH_2$— groups may be replaced by —CH=CH—,
  c) $R^4$ and $R^5$ together may alternatively be —$(CH_2)_4$— or —$(CH_2)_5$— if they are bonded to an oxirane, dioxolane, tetrahydrofuran, tetrahydropyran, butyrolactone or valerolactone system; with the proviso that $R^3$ can only be hydrogen if $R^3$is a substituent of one of the ring systems mentioned;

$M^1$ is —CO—O—, —$CH_2$—O—, —CH=CH—, —C≡C—, —$CH_2$—$CH_2$—CO—O—, —$CH_2CH_2CH_2CH_2$—, —$CH_2CH_2CH_2O$— and mirror-image arrangements thereof; or a single bond;

$A^1$ is 1,4-phenylene, in which one or more H atoms may be replaced by F, Cl and/or CN, 1,4-cyclohexylene, in which one or two H atoms may be replaced by CN and/or $CH_3$ and/or F, naphthalene-2,6-diyl, in which one or more H atoms may be replaced by F, Cl and/or CN; or a single bond.

The provision of compounds of the formula (I) very generally considerably broadens the range of liquid-crystalline substances which are suitable, from various applicational points of view, for the preparation of liquid-crystalline mixtures.

In this connection, the compounds of the formula (I) have a broad range of applications. Depending on the choice of substituents, they can be used as base materials of which liquid-crystalline phases are predominantly composed; however, it is also possible to add compounds of the formula (I) to liquid-crystalline base materials from other classes of compound in order, for example, to modify the dielectric and/or optical anisotropy of a dielectric of this type and/or to optimize its threshold voltage and/or its viscosity.

The compounds of the formula (I) are particularly suitable, even when added in small amounts, for influencing the dielectric anisotropy ($\Delta\epsilon$).

Utilizing this property, the compounds of the formula (I) according to the invention are particularly suitable for use in FLC mixtures operated in inverse mode. They are furthermore particularly suitable for use in mixtures based on ECB mode (electrically controlled birefringence). The compounds of the formula (I) are also particularly suitable for use in nematic and chiralsmectic mixtures developed for active matrix or super- TFT modes.

In a group of compounds which are particularly suitable for use in ferroelectric and ECB mixtures, the symbols and indices in the formula (I) have the following meanings:

$G_1$ is —CH=CH—;

$Y_1$ and $Y_2$ are H;

$X_1$, $X_2$, $X_3$ and $X_4$ are F (with the abovementioned provisos);

$R^1$ and $R^2$ are preferably identical or different and are
  a) a straight-chain or branched alkyl radical (with or without an asymmetrical carbon atom) having 1 to 18 carbon atoms, in which, in addition, one or more H atoms may be replaced by F and where
    a1) one or more non-adjacent and non-terminal —CH$_2$— groups may be replaced by —O—, —CO—O—, —O—CO—, —O—CO—O— or —Si(CH$_3$)$_2$—, and/or
    a2) one —CH$_2$— group may be replaced by cyclopropane-1,2-diyl, 1,4-phenylene or trans-1,4-cyclohexylene;

$R^1$ and $R^2$ are particularly preferably identical or different and are
  a1) a straight-chain or branched alkyl radical (with or without an asymmetrical carbon atom) having 1 to 16 carbon atoms, where
  a2) one non-terminal —CH$_2$— group may be replaced by —O—, and one or more H atoms may be substituted by F.

$M^1$ is preferably —CH$_2$CH$_2$—, —CH$_2$CH$_2$CH$_2$CH$_2$— or a single bond.

$M^1$ is particularly preferably a single bond.

$A^1$ is preferably 1,4-phenylene, trans-1,4-cyclohexylene or a single bond.

$A^1$ is particularly preferably a single bond.

This group includes, for example, the compounds (In), (Io), (Ip) and (Iq) shown below.

In a group of compounds which are particularly suitable for use in nematic liquid-crystal mixtures for active-matrix or super-TFT applications, the symbols and indices in the formula (I) have the following meanings:

$G_1$ is —CH=CH—;

$Y_1$ is F;

$Y_2$ is H;

$X_1$ is H or F;

$X_2$ is H or F;

$X_3$ is H;

$X_4$ is H;

$R^1$ is H, Cl, F, CF$_3$O, CH$_2$FO, CF$_3$ or a straight-chain alkyl radical having 1 to 5 carbon atoms;

$R^2$ is a straight-chain alkyl or alkoxy radical having 1 to 5 carbon atoms;

$M^1$ is a single bond;

$A^1$ is a single bond.

This group includes, for example, the compounds (Ig), (Ih), (Ii), (Ik), (IL), (Im), (In), (Io), (Ip), (Iq), (Ir), (Is), (It) and (Iu) shown below.

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use can also be made here of variants which are known per se, but are not mentioned here in great detail.

If desired, the starting materials can also be formed in situ by not isolating them from the reaction mixture, but instead immediately converting them further into the compounds of the formula (I).

The following schemes show by way of example a possible synthetic route for the compounds of the formula (I), although other processes are feasible and possible.

Scheme 1

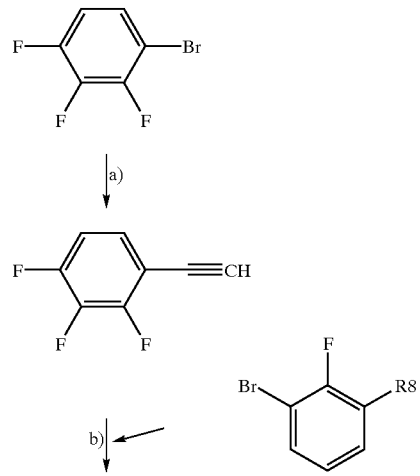

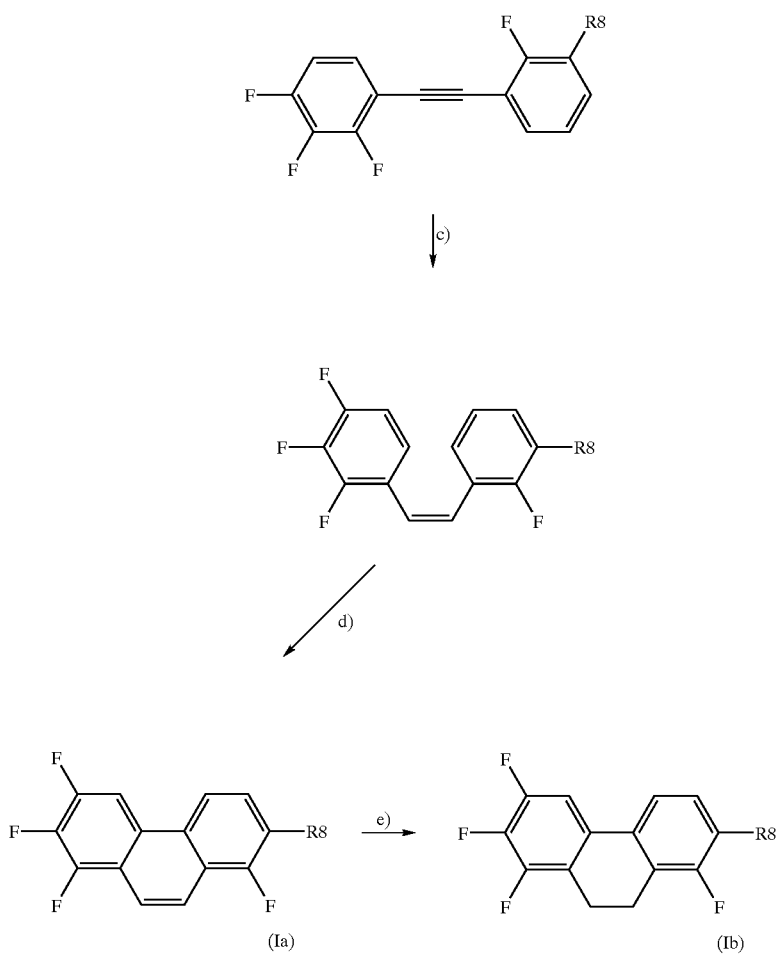

a) H—C≡C—TMS, HN(iPr)$_2$, Pd(II)/Cu(I) catalyst; e.g. J. Organomet. Chem. 453 (1993) 2, C19
b) HN(iPr)$_2$, Pd(O) catalyst; analogously to J. Organomet. Chem. 453 (1993) 2, C19
c) H$_2$/catalyst (P. N. Rylander, Hydrogenation Methods, Academic Press, London, 1985, p. 53)
d) Photocyclization (e.g. J. Am. Chem. Soc. 84, 4361 (1962))
e) H$_2$/Pd (C)

R$^8$: corresponds to R$^2$ or can be converted into R$^2$ by suitable subsequent reactions The 2,3,4-trifluorobromobenzene employed in Scheme 1 for the synthesis of (Ia) or (Ib) is commercially available; the synthesis of the 3-bromo-2-fluoro-R$^8$-phenyl derivative is described below. At the stage of photocyclization of 1-(2,3,4-trifluorophenyl)-2-(2-fluoro-3-R$^8$-phenyl)ethene, the (Z)-isomer is preferably employed; however, the (E)-isomer can also be employed since the (Z)-isomer is formed therefrom under the photocyclization conditions and can react in situ to form (Ia).

According to Scheme 2, the target structures (Ic), (Id), (Ie) and (If) can be obtained from 1-bromo-2,4,5-trifluorobenzene (commercially available) and the above-mentioned 3-bromo-2-fluoro-R$^8$-phenyl derivative. Analogously, Scheme 3 describes the synthesis of the target compounds (Ig), (Ih), (Ii) and (Ik) from 1-bromo-2,4-difluorobenzene, which is likewise commercially available.

The 1-bromo-2,3,4-trifluorobenzene mentioned at the beginning of Scheme 4 is commercially available; the reactions proceed essentially analogously to those already described in Schemes 1–3.

The 3,4-difluoroacetophenone required as starting material in Scheme 5 is also commercially available. The further conversion to the target products does not display any peculiarities deviating from the other synthetic routes. For the synthesis of the target compounds (Ip), (Iq), (Ir) and (Is), Scheme 6 starts from commercial 4-bromo-2-fluorophenol, which is converted into the corresponding methyl ether by standard methods (for example Williamson ether synthesis). At the stage of the target compound (Ip) or (Iq), the methyl group can be cleaved off (by standard methods, for example using hydrobromic acid/acetic acid). The resultant hydroxyphenanthrene. can be converted into the target compound (Ir) or (Is) by reaction with difluorocarbene generated in situ. Scheme 7 starts from commercial 4-bromo-2-chlorofluorobenzene, which makes the target compounds (It) and (Iu) accessible substantially analogously to the schemes described above.

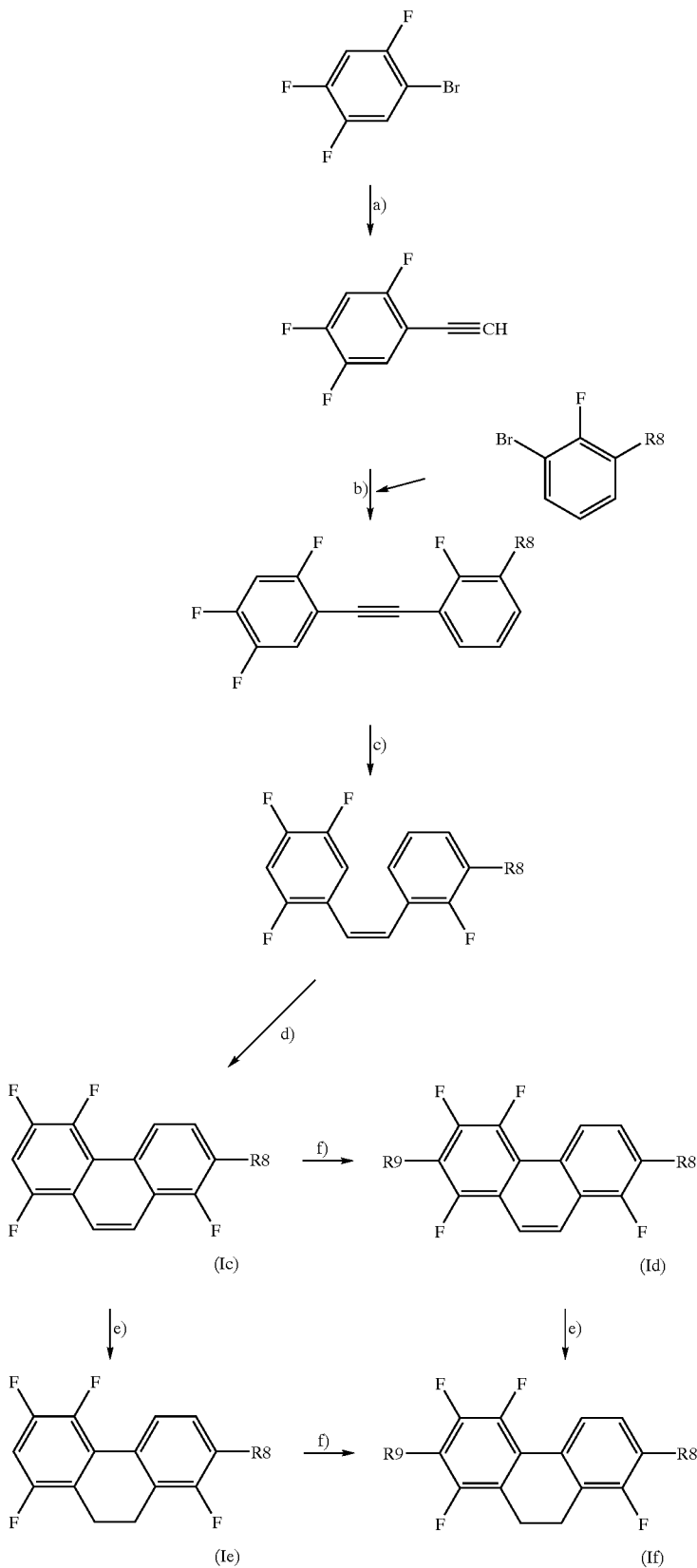

a) H—C≡C—TMS, HN(iPr)$_2$, Pd(II)/Cu(I) catalyst; e.g. J. Organomet. Chem. 453 (1993) 2, C19
b) HN(iPr)$_2$, Pd(O) catalyst; analogously to J. Organomet. Chem. 453 (1993) 2, C19
c) H$_2$/catalyst (P. N. Rylander, Hydrogenation Methods, Academic Press, London, 1985, p.53)
d) Photocyclization (e.g. J. Am. Chem. Soc. 84, 4361 (1962))
e) H$_2$/Pd (C)
f) 1. LDA 2. R$^9$—Br or 1. LDA 2. R—CHO 3. H+ 4. H$_2$ R$^8$: corresponds to R$^2$ or can be converted into R$^2$ by suitable subsequent reactions
R$^9$: corresponds to R$^1$ or can be converted into R$^1$ by suitable subsequent reactions
R: corresponds to the R$^9$ which is shorter by 1 carbon atom

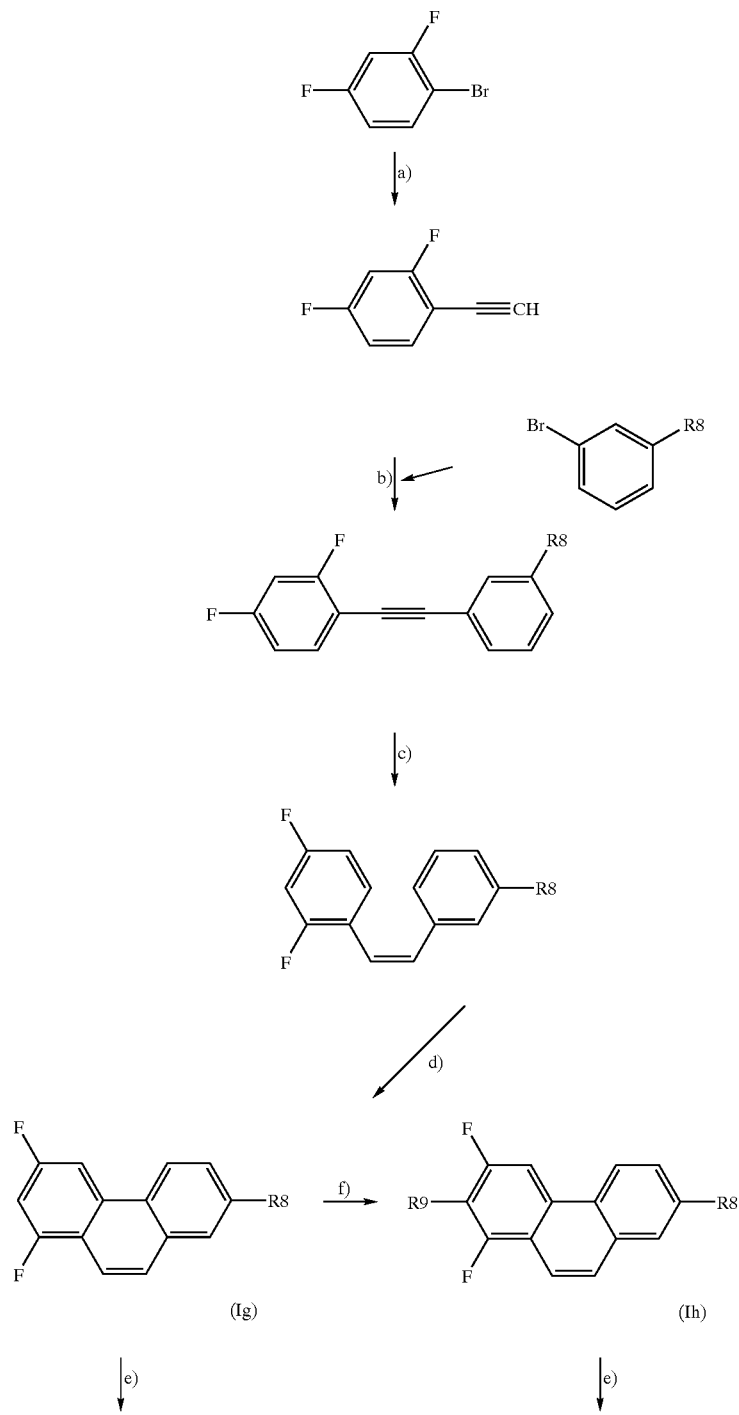

Scheme 3

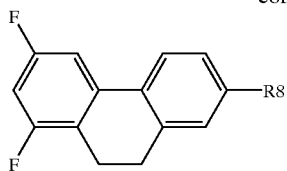

(Ii)

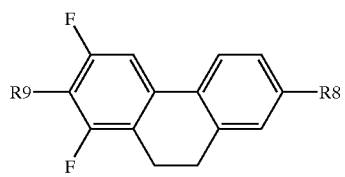

(Ik)

a) H—C≡C—TMS, HN(iPr)$_2$, Pd(II)/Cu(I) catalyst; e.g. J. Organomet. Chem. 453 (1993) 2, C19
b) HN(iPr)$_2$, Pd(O) catalyst; analogously to J. Organomet. Chem. 453 (1993) 2, C19
c) H$_2$/catalyst (P. N. Rylander, Hydrogenation Methods, Academic Press, London, 1985, p. 53)
d) Photocyclization (e.g. J. Am. Chem. Soc. 84, 4361 (1962))
e) H$_2$/Pd (C)
f) 1. LDA 2. R$^9$—Br or 1. LDA 2. R—CHO 3. H+4. H$_2$ R$^8$: corresponds to R$^2$ or can be converted into R$^2$ by suitable subsequent reactions
R$^9$: corresponds to R$^1$ or can be converted into R$^1$ by suitable subsequent reactions
R: corresponds to the R$^9$ which is shorter by 1 carbon atom Scheme 4

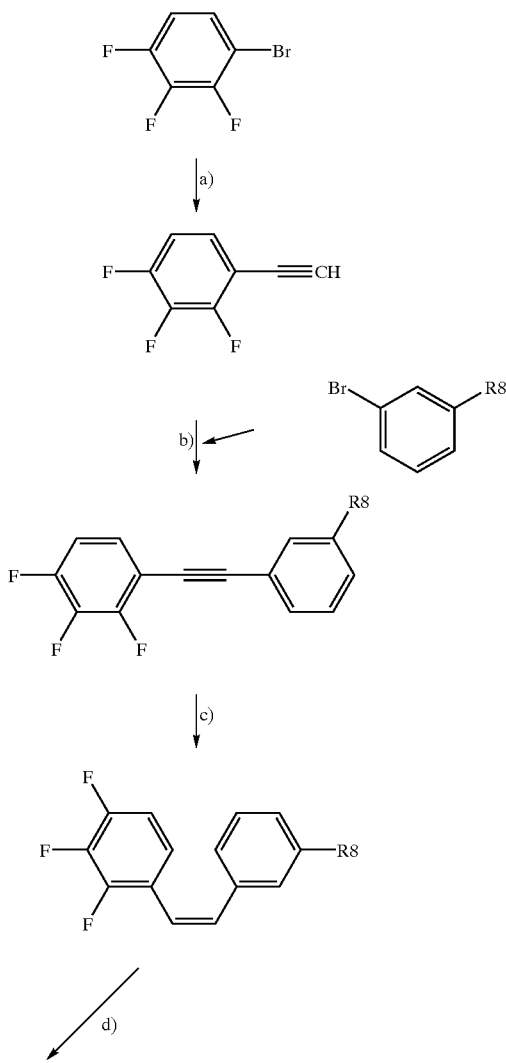

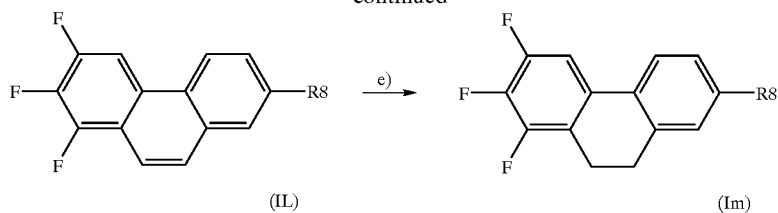
a) H—C≡C—TMS, HN(iPr)$_2$, Pd(II)/Cu(I) catalyst; e.g. J. Organomet. Chem. 453 (1993) 2, C19
b) HN(iPr)$_2$, Pd(O) catalyst; analogously to J. Organomet. Chem. 453 (1993) 2, C19
c) H$_2$/catalyst (P. N. Rylander, Hydrogenation Methods, Academic Press, London, 1985, p.53)
d) Photocyclization (e.g. J. Am. Chem. Soc. 84, 4361 (1962))
e) H$_2$/Pd (C)
R$^8$: corresponds to R$^2$ or can be converted into R$^2$ by suitable subsequent reactions
Scheme 5
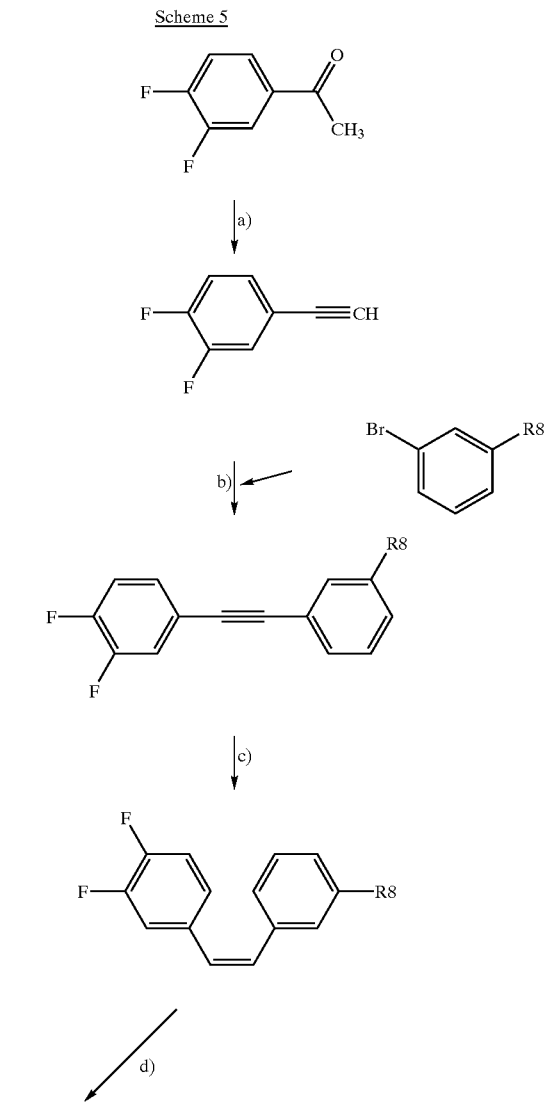

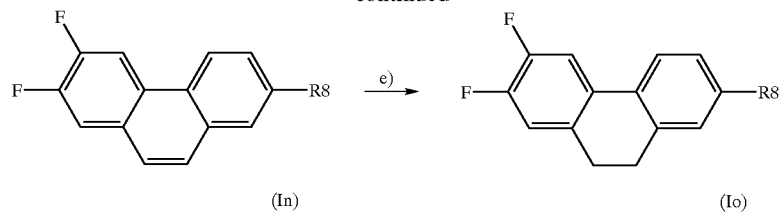
a) H—C≡C—TMS, HN(iPr)$_2$, Pd(II)/Cu(I) catalyst; e.g. J. Organomet. Chem. 453 (1993) 2, C19
b) HN(iPr)$_2$, Pd(O) catalyst; analogously to J. Organomet. Chem. 453 (1993) 2, C19
c) H$_2$/catalyst (P. N. Rylander, Hydrogenation Methods, Academic Press, London, 1985, p.53)
d) Photocyclization (e.g. J. Am. Chem. Soc. 84, 4361 (1962))
e) H$_2$/Pd (C)
R$^8$: corresponds to R$^{22}$ or can be converted into R$^2$ by suitable subsequent reactions
Scheme 6
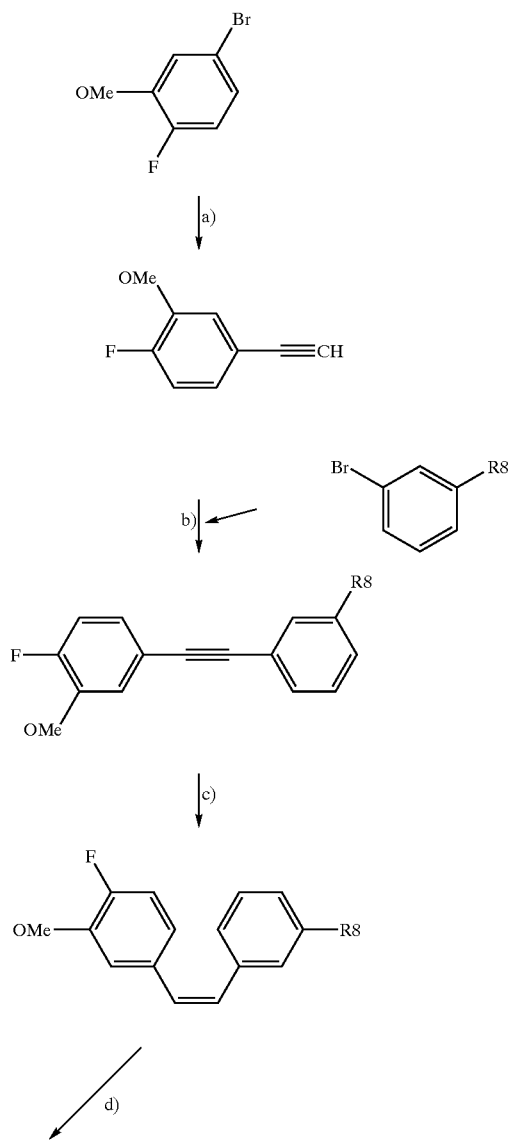

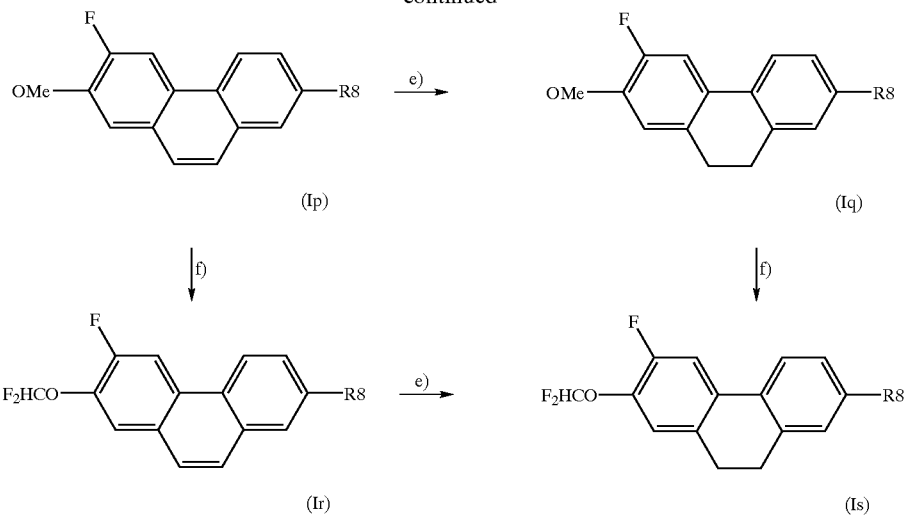

a) H—C≡C—TMS, HN(iPr)₂, Pd(II)/Cu(I) catalyst; e.g. J. Organomet. Chem. 453 (1993) 2, C19
b) HN(iPr)₂, Pd(0) catalyst; analogously to J. Organomet. Chem. 453 (1993) 2, C19
c) H₂/catalyst (P. N. Rylander, Hydrogenation Methods, Academic Press, London, 1985, p.53)
d) Photocyclization (e.g. J. Am. Chem. Soc. 84, 4361 (1962))
e) H₂/Pd (C)
f) 1. HBr/HOAc 2. CF₂Cl₂/base/phase-transfer catalyst $R^8$: corresponds to $R^2$ or can be converted into $R^2$ by suitable subsequent reactions Scheme 7

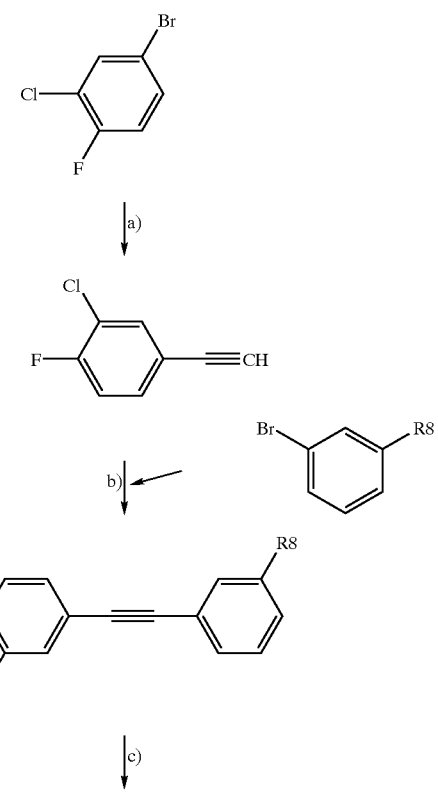

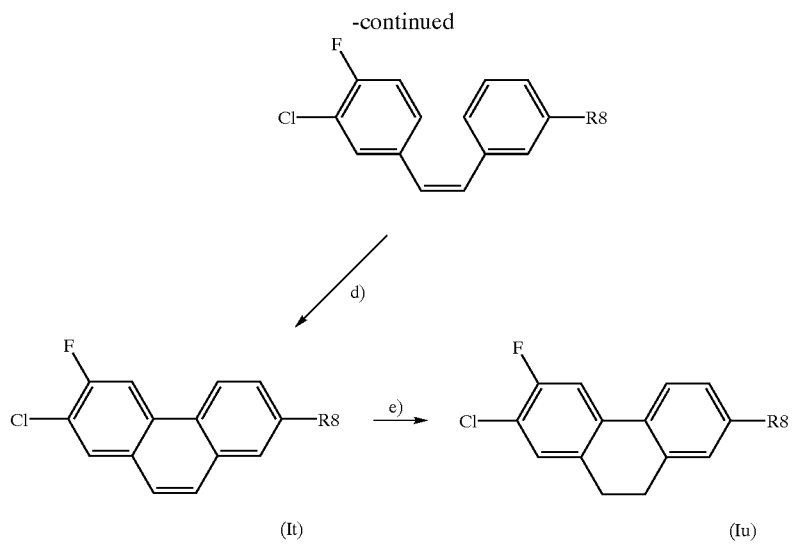

a) H—C≡C—TMS, HN(iPr)$_2$, Pd(II)/Cu(I) catalyst; e.g. J. Organomet. Chem. 453 (1993) 2, C19 b) HN(iPr)$_2$, Pd(0) catalyst; analogously to J. Organomet. Chem. 453 (1993)32, C19 c) H$_2$/catalyst (P. N. Rylander, Hydrogenation Methods, Academic Press, London, 1985, p. 53)

d) Photocyclization (e.g. J. Am. Chem. Soc. 84, 4361 (1962))

e) H$_2$/Pd (C)

R$^8$: corresponds to R$^2$ or can be converted into R$^2$ by suitable subsequent reactions In general, for the synthesis of the groups (—A$^1$—M$^1$), R$^1$ and —CH$_2$—R$^2$, reference may be made, for example, to DE-A 23 44 732, 24 50 088, 24 29 093, 25 02 94, 26 36 684, 27 01 591 and 27 52 975 for compounds containing 1,4-cyclohexylene and 1,4-phenylene groups.

Dioxane derivatives are advantageously prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures from about 20° C. to about 150° C., preferably from 80° C. to 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group with a fluorine atom, for example by the methods of Balz and Schiemann.

As far as the linking of ring systems to one another is concerned, reference may be made, for example to the following:

N. Miyaura, T. Yanagai and A. Suzuki in Synthetic Communications 11 (1981), 513–519, DE-C 39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821;

EP-A 0 354 434 and EP-A 0 694 530 for the direct linking of aromatics and heteroaromatics; DE-A 32 01 721 for compounds containing —CH$_2$CH$_2$—bridges, and Koji Seto et al. in Liquid Crystals 8 (1990) 861–870, for compounds containing —C≡C— bridging members.

Esters of the formula (I) can also be obtained by esterification of corresponding carboxylic acids (or reactive derivatives thereof) using alcohols or phenols (or reactive derivatives thereof, by the DCC method (DCC=dicyclohexylcarbodiimide) or analogously to DE-A 44 27 198. The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkali metal compound can then be reacted with the corresponding alkyl halide, alkyl sulfonate or dialkyl sulfate, advantageously in an inert solvent, such as acetone, 1,2-dimethoxyethane, DMF or dimethyl sulfoxide, or alternatively with an excess of aqueous or aqueous-alcoholic NaOH or KOH, at temperatures from about 20° to 100° C.

Regarding the synthesis of specific radicals $R^1$ and $R^2$ reference may additionally be made, for example, to EP-A 0 355 008 for compounds having silicon-containing side chains, EP-A 0 292 954 for optically active compounds containing an oxirane ester unit, EP-A 0 263 437 for optically active compounds containing an oxirane ether unit, EP-A 0 361 272 for optically active compounds containing a dioxolane ester unit, EP-A 0 351 746 for optically active compounds containing a dioxolane ether unit, U.S. Pat. No. 5,051,506 for optically active compounds containing a 2,3-difluoroalkoxy unit, U.S. Pat. No. 4,798,680 for optically active compounds containing a 2-fluoroalkoxy unit, U.S. Pat. No. 4,855,429 for optically active compounds containing an α-chlorocarboxyl unit, EP-A 0 552 658 for compounds containing cyclohexyl-propionyl radicals, and EP-A 0 318 423 for compounds containing cyclopropyl groups in the side chain.

The invention also relates to the use of compounds of the formula (I) in liquid-crystal mixtures, preferably smectic and nematic mixtures, particularly preferably ferroelectric and nematic mixtures. Particular preference is given to use in ferroelectric liquid-crystal mixtures operated in inverse mode and in nematic liquid-crystal mixtures for "active matrix", super-TFT-IPS and/or ECB applications.

The invention furthermore relates to liquid-crystal mixtures, preferably smectic and nematic mixtures, particularly preferably ferroelectric and nematic mixtures, comprising one or more compounds of the formula (I). The smectic or nematic liquid-crystal mixtures according to the invention are preferably suitable for use in electro-optical displays, in the case of nematic-mixtures particularly for "active matrix displays" and "in-plane switching displays" (IPS-LCDs), in the case of smectic liquid-crystal mixtures for ECB (electrically controlled birefringence) displays, for electroclinic displays and chiral tilted smectic (ferroelectric and antiferroelectric) displays.

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures comprising compounds of the formula (I) according to the invention are preferably selected from known compounds having smectic and/or nematic and/or cholesteric phases. These include, for example:

derivatives of phenylpyrimidine, as described, for example, in WO-A 86/06401 and U.S. Pat. No. 4,874,542, meta-substituted aromatic compounds having a six-membered ring, as described, for example, in EP-A 0 578 054, silicon compounds, as described, for example, in EP-A 0 355 008, mesogenic compounds having only one side chain, as described, for example, in EP-A 0 541 081, hydroquinone derivatives, as described, for example, in EP-A 0 603 786, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles, as described, for example, in EP-A 0 309 514.

Examples of suitable chiral, non-racemic dopants are the following:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A0 263 437. and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, optically active tetrahydrofuran-2-carboxylic esters, as described, for example, in EP-A 0 355 561, and optically active 2-fluoroalkyl ethers, as described, for example, in EP-A 0 237 007, EP-A 0 428 720 and U.S. Pat. No. 5,051,506.

Preferred further components of FLC mixtures employed in inverse mode are the following:

phenanthrene derivatives of the formula (II)

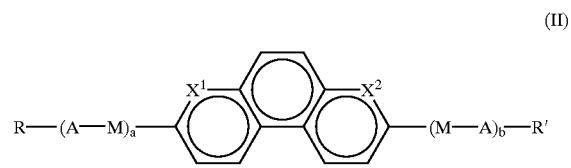

(II)

fluoropyridines of the formula (III)

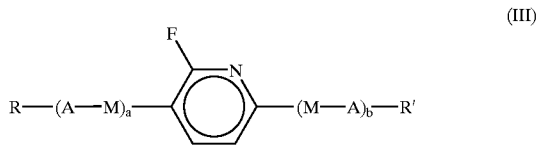

(III)

difluorophenylene derivatives of the formula (IV)

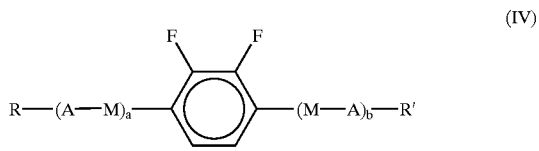

(IV)

meta-substituted aromatic compounds of the formula (V)

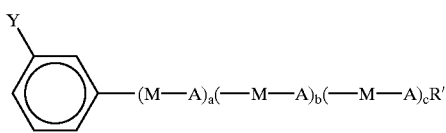

4-cyanocyclohexyls of the formula (VI)

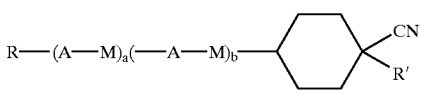

1,3,4-thiadiazoles of the formula (VII)

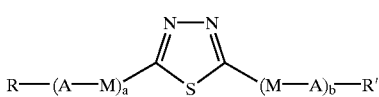

where the symbols and indices have the following meanings:
$X^1$ and $X^2$ are identical or different and are, independently of one another, CH, CF or N;
Y is F, $CF_3$ or R;
R and R' are identical or different and are, independently of one another, as defined for $R^1$ and $R^2$ in the formula (I);
A and M are identical or different and are, independently of one another, as defined in the formula (I), and
a, b, c and d are identical or different and are, independently of one another, 0 or 1, with the proviso that the compounds can contain not more than four ring systems and, with the exception of the formula (II), must contain at least two ring systems.

Suitable further constituents of nematic or chiral nematic liquid-crystal mixtures according to the invention are, for example,
4-fluorobenzenes, as described, for example, in EP-A 494 368, WO 92/06 148, EP-A 460 436, DE-A 4 111 766, DE-A 4 112 024, DE-A 4 112 001, DE-A 4 100 288, DE-A 4 101 468, EP-A 423 520, DE-A 392 3064, EP-A 406 468, EP-A 393 577 and EP-A 393 490,
3,4-difluobernzenes, as described, for example, in DE-A 4 108 448, EP-A 507 094 and EP-A 502 407,
3,4,5-trifluorobenzenes, as described, for example, in DE-A 4 108 448 and EP-A 387 032,
4-benzotrifluorides, as described, for example, in DE-A 4 108 448,
phenylcyclohexanes, as described, for example, in DE-A 4 108 448.

The mixtures can in turn be used in electro-optical or fully optical elements, for example display elements, switching elements, light modulators, elements for image processing and/or signal processing or generally in the area of nonlinear optics.

The mixtures are furthermore suitable for field treatment, i.e. for operation in the quasi-bookshelf geometry (QBG) (see, for example, H. Rieger et al., SID 91 Digest (Anaheim) 1991, 396).

The ferroelectric liquid-crystal mixtures according to the invention are particularly suitable for operation in so-called inverse or $\tau V_{(min)}$ mode (see, for example, J. C. Jones, M. J. Towler, J. R. Hughes, Displays 1993, 14, No. 2, 86–93; M. Koden, Ferroelectrics 1996,179,121–129).

Liquid-crystalline mixtures comprising compounds of the general formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting plate (for example of glass). In addition, they can contain spacer!, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

The invention therefore furthermore relates to a switching and/or display device, preferably a smectic or nematic switching and/or display device, in particular a ferroelectric switching and/or display device, containing a liquid-crystal mixture comprising one or more compounds of the formula (I). In devices which contain a nematic liquid-crystal mixture, active matrix displays and in-plane switching displays (IPS-LCDs) are preferred.

In devices which contain a smectic liquid-crystal mixture, ECB (electrically controlled birefringence) displays, electroclinic displays and chiral tilted smectic (ferroelectric or antiferroelectric) displays are preferred.

Such displays can be used, for example, as computer displays or in smart cards.

A ferroelectric switching and/or display device according to the invention is preferably operated in normal or inverse mode.

Ferroelectric switching and/or display devices operated by multiplex addressing can be operated, inter alia, in two different modes, so-called normal mode or so-called inverse mode ($\tau V_{(min)}$ mode). The difference between the two is in the addressing scheme and in the different requirements made of the dielectric tensor of the FLC material, i.e. of the FLC mixture. An overview is given, for example, by J. C. Jones et al. in Displays 1993, 14, No. 2, 86–93, referred to below as "Jones", and in M. Koden in Ferroelectrics 1996, 179, 121–129, and the literature cited therein.

The switching characteristics of an FLC device can generally be represented by a diagram in which the driving voltage (V) is plotted on the horizontal axis and the width of the addressing pulses ($\tau$, time) is plotted on the vertical axis (see, for example, Jones, FIGS. 4, 8, 10 and 11).

A switching curve is determined experimentally and divides the V,$\tau$ area into a switching region and a non-switching region. The pulse width usually shortens when the voltage is increased. This behavior characterizes so-called normal mode (see, for example, Jones, FIG. 4).

In suitable materials, however, the VT curve has a minimum (at voltage $V_{(min)}$), as shown, for example, in Jones in FIGS. 8, 10 and 11. This minimum arises from superposition of dielectric and ferroelectric twist. FLC devices are operated in inverse mode if the sum of the row and column driving voltages in the operating temperature range is greater than the minimum on the V$\tau$ curve, i.e. $V_{(row)} + V_{(column)} > V_{(min)}$.

In the present application, various documents are cited, for example in order to illustrate the technical background to the invention. All these documents are expressly incorporated herein by way of reference.

The invention likewise relates to novel ethyne derivatives of the formula

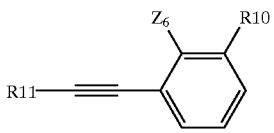

in which:
R10 is an alkyl or alkoxy radical having 1 to 16 carbon atoms,
R11 is H if $Z_6$ is F; or

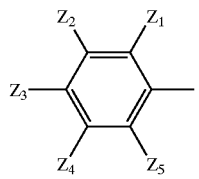

in which:
a) $Z_1$ is F; $Z_2$ is alkyl or alkoxy having 1 to 16 carbon atoms; $Z_3$, $Z_4$ and $Z_5$ are H; $Z_6$ is F
b) $Z_1$, $Z_2$ and $Z_3$ are F; $Z_4$ and $Z_5$ are H; $Z_6$ is F
c) $Z_1$ and $Z_3$ are F; $Z_2$ is H; $Z_4$ and $Z_5$ are H; $Z_6$ is F
d) $Z_1$ and $Z_3$ are F; $Z_2$ is H; $Z_4$ and $Z_5$ are H; $Z_6$ is H
e) $Z_2$ and $Z_3$ are F; $Z_1$ is H; $Z_4$ and $Z_5$ are H; $Z_6$ is H
f) $Z_1$, $Z_2$ and $Z_3$ are F; $Z_4$ and $Z_5$ are H; $Z_6$ is H
g) $Z_1$ is H; $Z_2$ is Cl; $Z_3$ is F; $Z_4$ and $Z_5$ are H; $Z_6$ is H.

In the preferred process for the preparation of the compounds of the formula (I), they have a key function since on the one hand they can be hydrogenated to the corresponding ethene derivatives (which are themselves photocyclized; see above Schemes 1–7) in very good yields and high purities without the production of substantial amounts of by-products, and on the other hand are accessible in high yields and very good purities in a convergent reaction which easily facilitates homologization.

It has been found that this reaction sequence 1-aryl-2-aryl'-ethyne-1-aryl-2-aryl'-ethene—photocyclization is not only particularly suitable for the phenanthrene derivatives according to the invention, but is also particularly suitable for the preparation of phenanthrene derivatives having a different substitution pattern of electronegative radicals (as described, for example, in U.S. Pat. No. 5,648,021 or DE-A 19524230 with still other preparation processes therein).

The invention likewise relates to boronic acid derivatives of the formula

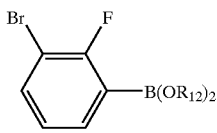

in which:
$R_{12}$ is H or alkyl having 1 to 10 carbon atoms, preferably H, with the understanding that the cyclic anhydride which forms in the case where $R_{12}$=H is likewise according to the invention. In the preparation of this compound, a mixture of boronic acid and the cyclic anhydride thereof is usually formed, but this does not cause problems either for Suzuki couplings or for oxidation to the phenol, since both the mixture and each of the individual components undergoes the relevant reactions.

The invention likewise relates to a process for the preparation of 3-bromo-2-fluorophenol starting from 3-bromo-2-fluorophenylboronic acid. Compared with other feasible processes (for example nucleophilic substitution of one of the bromine atoms of 2,6-dibromofluorobenzene), this process is distinguished by high regioselectivity, good yield and high purity.

The invention is explained in greater detail by the following examples, without this being intended to represent a limitation.

EXAMPLE 1

6-Fluoro-2-methyl-7-methoxyphenanthrene

4-Bromo-2-methoxyfluorobenzene (obtainable from 5-bromo-2-fluorophenol by reaction with dimethyl sulfate under basic conditions) is reacted with trimethylsilylacetylene with catalysis by bis(triphenylphosphine)palladium(II) chloride and copper(I) iodide in dimethylamine at 20° C. to give 1-(4-fluoro-3-methoxyphenyl)-2-(trimethylsilyl)ethyne; after filtration chromatography (SiO$_2$/dichloromethane), the crude product is stirred in methanol for 1 hour at 20° C. with addition of 1 N aqueous NaOH solution. Removal of the solvent by distillation and chromatography (SiO$_2$/dichloromethane) gives 4-ethynyl-3-methoxyfluorobenzene.

The latter is stirred for 10 hours at 20° C. in 30 times the amount (by volume) of benzene with 3-methylbromobenzene and tetrakis(triphenylphosphine)palladium(0) [as catalyst] and n-propylamine. Removal of the volatile constituents by distillation under reduced pressure gives 1-(4-fluoro-3-methoxyphenyl)-2-(3-methylphenyl)ethyne. Dissolved in 50 times the amount of tetrahydrofuran (anhydrous), the latter is hydrogenated using Lindlar catalyst (Org. Synthesis 46, 89 (1966)) to give (Z)-1-(4-fluoro-3-methoxyphenyl)-2-(3-methylphenyl)ethene; a small content of (E)-isomer does not interfere with the performance of the remainder of the reaction.

After chromatography (SiO$_2$/dichloromethane), this intermediate is dissolved in cyclohexane (500 ml/g of intermediate) and exposed to UV light for 15 hours in a quartz apparatus with addition of 4 mol % of iodine. Chromatography (SiO$_2$/dichloromethane) and recrystallization from acetonitrile gives the target compound.

The other compounds of the formula (I) can also be obtained analogously, it also being possible to use variants of individual reaction steps.

EXAMPLE 2

6-Fluoro-2-methyl-7-octyloxyphenanthrene can be obtained analogously to Example 1 by reacting 5-bromo-2-fluorophenol with octyl bromide to give 4-bromo-2-octyloxyfluorobenzene. It is also possible to subject the compound from Example 1 to ether cleavage (for example using hydrobromic acid/acetic acid) and to etherify the resultant phenol using octyl bromide.

EXAMPLE 3

2-Hexyloxy-1,6,7,8-tetrafluorophenanthrene 290 ml of a 1.6 molar solution of butyllithium in hexane are added dropwise at −70° C. to a solution of 112 g of 2,6-dibromofluorobenzene [1435-54-7] in 1000 ml of diethyl ether. After the mixture has been kept at the same temperature for 2 hours, 60 ml of trimethyl borate are added, and the mixture is stirred at this temperature for 12 hours. After the mixture has been slowly warmed to room temperature, 300 ml of water are added, and the pH is adjusted to 1 by addition of hydrochloric acid. The organic phase is separated off, the aqueous phase is extracted twice with 100 ml of ether each time, and the combined organic phases are dried under reduced pressure, giving 91 g of 3-bromo-2-fluorophenylboronic acid (mixed with its cyclic anhydride) as a brown solid; $^1$H-NMR (DMSO-$d_6$): 7.1–7.7 (m) ppm, $^{19}$F-NMR (DMSO-$d_6$): –99 ppm.

125 ml of a 35% strength aqueous solution of hydrogen peroxide are added dropwise at room temperature to the crude 2-bromo-1-fluorophenylboronic acid (80 g) dissolved in 300 ml of tert-butyl methyl ether; during this addition, the temperature rises to 55° C. When the addition is complete, the mixture is refluxed for a further 2 hours. After the mixture has been cooled, 100 ml of water are added, and the organic phase is extracted by shaking twice with saturated sodium sulfite solution. After the solvent has been removed by distillation under reduced pressure, vacuum distillation (90° C.; 4 mbar) gives 54 g of 3-bromo-2-fluorophenol as an oil which soon crystallizes. $^1$H-NMR (CDCl$_3$): 6.9–7.1 (m; 3H); 5.1 (br; 1H), $^{19}$F-NMR (CDCl$_3$): –135 ppm.

117 g of potassium carbonate and 55.6 g of bromohexane are added to a solution of 53.6 g of 3-bromo-2-fluorophenol in 650 ml of acetone, and the mixture is refluxed for 8 hours. The mixture is filtered, evaporated to ⅓ of the original volume and poured into 600 ml of water. The pH is adjusted to 1 using hydrochloric acid, and the mixture is extracted three times with 150 ml of tert-butyl methyl ether each time. The combined organic phases are concentrated under reduced pressure, and the residue is subjected to vacuum distillation (103° C.; 1 mbar), giving 67 g of 6-bromo-2-hexyloxyfluorobenzene as a colorless oil. $^1$H-NMR (CDCl$_3$): 6.9–7.1 (m; 3H); 4.0 (t; 2H), 0.9–1.8 (m, 11H), $^{19}$F-NMR (CDCl$_3$): –128 ppm. A solution of 67.3 g of 6-bromo-2-hexyloxyfluorobenzene, 24.7 g of 2-methyl-3-butyn-2-ol [115-19-5], 0.7 g of bis(triphenylphosphine) palladium(II) chloride and 0.7 g of copper iodide in 340 ml of triethylamine is refluxed for 5 hours. The mixture is then poured into 1.5 of ice-water, the pH is adjusted to 1 using hydrochloric acid, and the mixture is extracted three-times with 200 ml of tert-butyl methyl ether each time. The combined organic phases are dried under reduced pressure. The crude 4-(2-fluoro-3-hexyloxyphenyl)2methyl-3-butyn-1-ol is refluxed for 3 hours in 1000 ml of toluene together with three mole-equivalents of sodium hydroxide. The mixture is filtered and washed with dilute hydrochloric acid, the solvent is removed by distillation, and the residue is distilled (90° C.; 0.5 mbar), giving 34 g of 1-(2-fluoro-3-hexyloxyphenyl)ethyne.

$^1$H-NMR (CDCl$_3$): 7.0 (m; 3H); 4.0 (t; 2H), 3.3 ("s"; 1H), 0.9–1.8 (m, 11H), $^{19}$F-NMR (CDCl$_3$): –132 ppm.

Reaction thereof with 2,3,4-trifluorobromobenzene to give 1-(2-fluoro-3-hexyloxyphenyl)-2-(2,3,4-trifluorophenyl)ethyne, followed by hydrogenation thereof to give 1-(2-fluoro-3-hexyloxyphenyl)-2-(2,3,4-trifluorophenyl)ethene and photocyclization were carried out analogously to Example 1.

What is claimed is:
1. A fluorinated phenanthrene derivative of the formula (1)

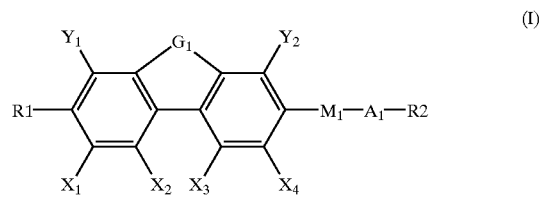

where the symbols and indices are defined as follows:

$G_1$ is —H=CH— or —CH$_2$CH$_2$—;

$X_1$, $X_2$, $X_3$ and $X_4$, independently of one another, are H of F, with the provisos that
a) $X_1$, $X_2$, $X_3$, $X_4$ are not simultaneously H
b) $X_1$, $X_2$, $X_3$, $X_4$ are not simultaneously F $Y_1$ and $Y_2$, independently of one another, are H or F;

$R^1$ and $R^2$ are identical or different and are
a) a straight-chain or branched alkyl radical (with or without an asymmetrical carbon atom) having 1 to 20 carbon atoms, in which, in addition, one or more H atoms may be replaced by F and where
a1) one At more non-adjacent and non-terminal —CH$_2$— groups may be replaced by —O—, —S—, —CO—O—, —O—CO—, —O—CO—O— or —Si(CH$_3$)$_2$—, and/or
a2) one or more —CH$_2$— groups may be replaced by —CH=CH—, —C≡C—, cyclopropane1,2-diyl, 1,4-phenylene, 1,4-cyclohexylene or 1,3-cyclopentylene, and/or
a3) the terminal —CH$_3$ group may be replaced by one of the following chiral groups (optically active: or racemic):

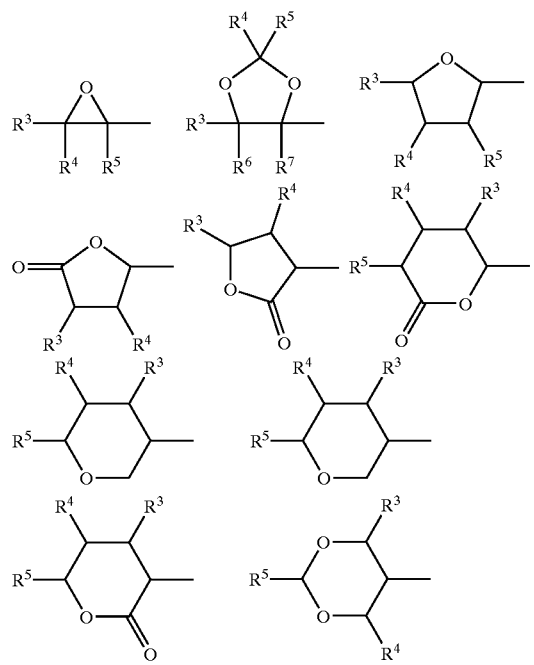

-continued

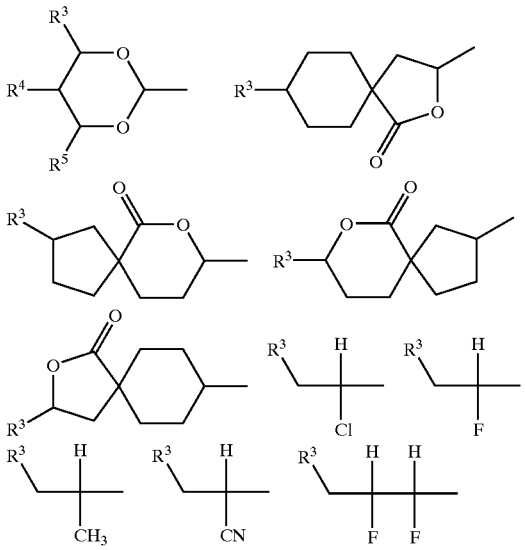

$R^1$ is alternatively hydrogen, —OCF$_3$, —CF$_3$, —CN, —F, —Cl, —OCHF$_2$, —OCH$_2$F, —CHF$_2$ or —CH$_2$F;

b) $R^1$ is alternatively hydrogen, Cl or F;

$R^3$, $R^4$, $R^5$, $R^6$ and $R^7$ are identical or different and are a) hydrogen b) a straight-chain or branched alkyl radical (with or without an asymnmetrical carbon atom) having 1 to 16 carbon atoms, where b1) one or more nonadjacent and non-terminal —CH$_2$— groups may be replaced by; —O—; and/or b2) one or two —CH$_2$— groups may be replaced by —CH═CH—, c) $R^4$ and $R^5$ together may alternatively be —(CH$_2$)$_4$— or —(CH$_2$)$_5$— if they are bonded to an oxirane, dioxolane, tetrahydrofuran, tetrahydropyran, butyrolactone or valerolactone system;

with the proviso that $R^3$ can only be hydrogen If $R^3$ is a substituents of one of the ring systems mentioned;

$M^1$ is —CO—O—, —CH$_2$—O—, —CH═CH—, —C≡C—, —CH$_2$—CH$_2$—CO—O—, —CH$_2$CH$_2$CH$_2$CH$_2$—, —CH$_2$CH$_2$CH$_2$O— and mirror-image arrangements thereof or a single bond;

$A^1$ is 1,4-phenylene, in which one or more H atoms may be replaced by F, Cl and/or CN, 1,4-cyclohexylene, in which one or two H atoms may be replaced by CN and/or CH$_3$ arKdor F, naphthalene-2,6-diyl, in which one or more H atoms may be replaced by F, Cl and/or CN; or a single bond.

2. A fluorinated phenanthrene derivative as claimed in claim 1 wherein the symbols and indices in the formula (1) have the following meanings, $G_1$ is —CH═CH—;

$Y_1$ is F;

$Y_2$ is H;

$R^1$ is H, Cl, F, CF$_3$O, CH$_2$FO, CF$_3$ or a straight-chain alkyl radical having 1 to 5 carbon atoms;

$R^2$ is a straight-chain alkyl or alkoxy radical having 1 to 5 carbon atoms:

$M^1$ is a single bond;

$A^1$ is a single bond.

3. A liquid-crystal mixture comprising one or more compounds of the formula (I) as claimed in claim 1.

4. A liquid-crystal mixture as claimed in claim 3 which is chiral tilted smectic.

5. A liquid-crystal mixture as claimed in claim 3 which is nematic.

6. A liquid-crystal mixture as claimed in claim 4 which comprises from 0.01 to 80% by weight of one or more derivatives of the formula (I).

7. A liquid-crystal mixture as claimed in claim 3 which comprises from 0.01 to 80% by weight of one or more derivatives of the formula (I).

8. A switching device containing a liquid-crystal mixture as claimed in claim 6.

9. A display device containing a liquid-crystal mixture as claimed in claim 6.

10. A switching and display device containing a liquid-crystal mixture as claimed in claim 6.

11. A switching device containing a liquid-crystal mixture as claimed in claim 7.

12. A display device containing a liquid-crystal mixture as claimed in claimed 7.

13. A switching and display device containing a liquid-crystal mixture as claimed in claim 7.

14. A switching device in the form of a ferroelectric switching device containing a chiral tilted smectic liquid-crystal mixture as claimed in claim 4.

15. A display device in the form of an active-matrix display device containing a liquid-crystal mixture as claimed in claim 4.

16. A display device in the form of an active-matrix display device containing a liquid-crystal mixture as claimed in claim 5.

17. A display device in the form of a super-TFT (IPSI) display device containing a nematic liquid-crystal mixture as claimed in claim 5.

18. A display device in the form of an ECB display device containing a nematic liquid-crystal mixture as claimed in claim 5.

19. A monostable ferroelectric active-matrix display containing a liquid-crystal mixture as claimed in claim 4.

20. A boronic acid derivative of the formula

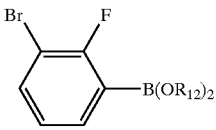

in which $R_{12}$ is H or alkyl having 1 to 10 carbon atoms, with the understanding that the cyclic anhydride which forms in the case where $R_{12}$=H is likewise according to the invention.

21. A process for the preparation of 3-bromo-2-fluorophenol, which comprises reacting 3-bromo-2-fluorophenylboronic acid with oxidants at temperatures of from 40 to 80° C.

22. An ethyne derivative of the formula

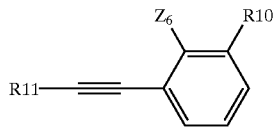

in which:

R10 is an alkyl or alkoxy radical having 1 to 16 carbon atoms,

R11 is H if $Z_6$ is F; or

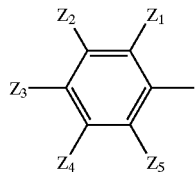

in which:
a) $Z_1$ is F; $Z_2$ is alkyl or alkoxy having 1 to 16 carbon atoms; $Z_3$, $Z_4$ and $Z_5$ are H; $Z_6$ is F
b) $Z_1$, $Z_2$ and $Z_3$ are F; $Z_4$ and $Z_5$ are H; $Z_6$ is F
c) $Z_1$ and $Z_3$ are F; $Z_2$ is H; $Z_4$ and $Z_5$ are H; $Z_6$ is F
d) $Z_1$ and $Z_3$ are F; $Z_2$ is H; $Z_4$ and $Z_5$ are H; $Z_6$ is H
e) $Z_2$ and $Z_3$ are F; $Z_1$ is H; $Z_4$ and $Z_5$ are H; $Z_6$ is H
f) $Z_1$, $Z_2$ and $Z_3$ are F; $Z_4$ and $Z_5$ are H; $Z_6$ is H
g) $Z_1$ is H; $Z_2$ is Cl; $Z_3$ is F; $Z_4$ and $Z_5$ are H; $Z_6$ is H.

\* \* \* \* \*